United States Patent [19]
Faso

[11] 4,217,664
[45] Aug. 19, 1980

[54] PROSTHESIS AND METHOD FOR CREATING A STOMA

[76] Inventor: Joseph M. Faso, 518 Montmarc Dr., Erie, Pa. 16508

[21] Appl. No.: 8,492

[22] Filed: Feb. 2, 1979

[51] Int. Cl.² ............................ A61F 1/00; A61F 5/44
[52] U.S. Cl. ............................................. 3/1; 128/1 R; 128/283; 128/348; 128/350 R
[58] Field of Search ....... 3/1; 128/283, 1 R, DIG. 25, 128/334 C, 348, 350 R

[56] References Cited

U.S. PATENT DOCUMENTS

| | | | |
|---|---|---|---|
| 3,216,420 | 11/1965 | Smith et al. ................... | 128/283 |
| 3,565,073 | 2/1971 | Giesy ............................. | 128/283 |
| 3,633,585 | 1/1972 | McDonald, Jr. ................ | 128/348 |
| 3,646,616 | 3/1972 | Keshin ........................... | 3/1 |
| 3,663,965 | 5/1972 | Lee, Jr. et al. ................ | 3/1 |
| 3,783,868 | 1/1974 | Bokros ........................... | 3/1 X |
| 3,818,511 | 6/1974 | Goldberg et al. .............. | 3/1 |
| 4,121,589 | 10/1978 | McDonnell ..................... | 128/283 |

OTHER PUBLICATIONS

"Carbon Urinary Conduits—Animal Experiments" by J. R. Longley et al., Prac. Animal Meet., American Urologist Association, 1977, pp. 1-6.

"The Quest for Continence: A Morphologic Survey of Approaches to a Continent Colostomy" by J. B. Tenney et al., American Society of Colon and Rectal Surgeons, vol. 21, No. 7, 1978 pp. 522-533.

*Primary Examiner*—Ronald L. Frinks

[57] ABSTRACT

A prosthesis and a method for implantation of a prosthesis in the body to cooperate with a body duct to provide a stoma. The prosthesis is particularly characterized by a mesh sleeve, a relatively rigid spout having a proximal end disposed in an opening in the body and a distal end projecting outside of the surface of the body. A layer of biocompatible mesh on the inside of the spout is disposed to engage the serosa of a portion of the body duct to promote growth of the body duct into the layer of mesh to anchor the body duct to the tubular spout. The mesh sleeve is preferably connected with the proximal end of the spout and is wrapped about the body duct and secured to the body wall to allow the serosa of the body duct to grow into the mesh to further anchor the body duct to the body wall. In a preferred embodiment, a fenestrated flange is disposed around the proximal end of the spout, and a removable cap is provided for closing and sealing the spout.

18 Claims, 8 Drawing Figures

PROSTHESIS AND METHOD FOR CREATING A STOMA

FIELD OF THE INVENTION

This invention relates to an improved prosthesis and a method for implanting a prosthesis in a body wall for cooperating with a body duct, such as the colon, ileum, urethra, portions of the vascular system, etc. to provide a stoma.

BACKGROUND OF THE INVENTION AND PRIOR ART

In completing a surgical procedure such as a colostomy or an ileostomy it is common to create a stoma to provide a conduit for allowing elimination of waste material from the patient's body. A well known procedure for creating the stoma is to direct a portion of body duct such as the colon or ileum through an opening in the patient's abdominal wall and to suture the body duct to the skin surrounding the opening. A flexible bag appended to the patient's body collects and retains liquid, solid and gaseous waste material eliminated through the stoma.

U.S. Pat. No. 3,565,073 shows such a procedure for creating a stoma, and also shows one way of appending the flexible bag to the patient's body. A magnet implanted beneath the patient's skin (cutaneous layer) attracts a magnetic ring to which the flexible bag is secured.

Another way of appending a bag to a patient's body is by means of an adhesive and gummy sealant about the stoma to hold and seal the device to the skin of the patient. Such materials have been found to cause irritation of the skin about the stoma and discomfort to the patient. Belts have also been used to hold the bag tightly against the stoma. However, belts have not been satisfactory in obviating the need for adhesives.

With a flexible bag appended to the patient's body passage of waste material into the bag is generally uncontrollable and may also be embarrassingly audible and otherwise detectable. Also, the bag may become uncomfortable as it fills with waste material.

Additionally, stomas created by the above-described procedures are often subject to postoperative problems, some of which can become serious enough to require postoperative treatment or further surgery.

For example, colostomy stomas are sometimes subject to postoperative herniation. A weak spot in the abdominal wall may occur at the point where the colon passes into the abdominal wall. Herniation may occur by the small or large intestine being forced into the abdominal wall at that weak spot. Such herniation can result in a serious blockage, and/or discomfort requiring surgery to correct it.

Another problem which may be experienced with a stoma created by the above-described procedure is postoperative prolapse of the colon or ileum. This can occur when intraabdominal pressure forces the colon or ileum to literally turn inside out and protrude in such a manner as to prolapse internal sections of the colon or ileum through the opening in the body wall. Again, surgery may be necessary to correct such a problem.

Still further, a potential problem with a stoma created by the above-described procedure is postoperative stricture forming in the stoma particularly at about the cutaneous (skin) level. Surgery may also be necessary to correct this problem.

A still further potential problem is serositis or inflamation of the serosa of the colon or ileum due to exposure of the body duct to air. This problem is particularly acute in stomas which are formed by suturing the colon or ileum directly to the skin surrounding the opening in the abdominal wall and especially when serosal surface is exposed to air. Serious inflamation can require treatment, or even surgery.

The foregoing types of problems may become serious enough to dictate corrective surgery, and may even require creation of a new stoma in a different location. Thus, there is always a possibility that a stoma created by such procedures may not be a permanent stoma.

A prior art device which has been suggested for implantation in the patient's body is disclosed in U.S. Pat. No. 3,646,616 (Keshin). The patent discloses a prosthesis for implantation around the urethra and various methods of treating urinary incontinence. The prosthesis includes a flexible mesh of biocompatible material implanted in a portion of body tissue about the urethra and having a resilient portion outside of the body coated with a water resistant coating. The patent discloses that the resilient portion outside of the body can be closed by a removable cap. The patent broadly suggests that the device could be used for colostomies or ileostomies, but does not disclose how the device could be so used. Also, the disclosed device, if used in a colostomy or ileostomy appears, nevertheless, subject to certain of the problems of prior art stomas such as for example, postoperative herniation, stricture of the duct, prolapse, etc.

Other types of devices designed for implantation in a patient's body are discussed in a paper entitled "Carbon Urinary Conduits—Animal Experiments" by Longley et al., Prac. Animal Meet. American Urologists Association 1977, and also in a paper entitled "The Quest for Continence" by Tenney et al., American Society of Colon and Rectal Surgeons, Vol. 21, No. 7, 1978. The papers both disclose a vitreous carbon conduit implant for a bladder vesicostomy; the latter paper further discloses a carbon conduit having a fenestrated flange thereon.

BRIEF STATEMENT OF THE INVENTION

Briefly stated, the present invention contemplates a prosthesis and a method of implanting a prosthesis in a body wall to cooperate with a body duct to provide a stoma.

The invention provides a stoma designed to minimize the likelihood of postoperative problems requiring corrective surgery, or even replacement of the stoma. Thus, there is provided a more permanent stoma than has been previously attainable. Additionally, it provides a stoma which is selectively closed and sealed in a manner which may eliminate the necessity for the patient wearing an appended bag, and which may reduce the embarrassment and discomfort associated therewith.

The preferred embodiment of the prosthesis according to the invention is characterized by a sleeve of flexible biocompatible mesh material which is desirably longitudinally split. A nonporous tubular spout of relatively rigid construction is also formed of a biocompatible material and has a proximal end connected with the flexible sleeve of mesh material. A layer of biocompatible mesh material is disposed on the inside of the tubular spout.

In creating a stoma, the proximal end of the tubular spout is implanted in an opening in the body wall with a distal end of the spout protruding outwardly from the body wall. A body duct, such as the colon or ileum, is passed through the opening in the body wall and into the tubular spout to bring it into contact with the layer of mesh on the inside of the spout. This allows the serosa of the duct to grow into the layer of mesh material. The flexible sleeve of mesh material is wrapped around the remainder of the body duct extending through the opening in the body wall, and the inner end of the sleeve of mesh is sutured to the inner surface of the body wall which surrounds the opening. This maintains the mesh in contact with the serosa of the remainder of the body duct, thereby allowing the serosa to grow into the flexible mesh. The spout may be closed and sealed by a suitable cap or plug which may be threadedly secured, for example, to the spout for selective removal therefrom.

A relatively rigid flange of biocompatible material is preferably attached to the proximal end of the tubular spout. When the spout is implanted in the body wall the flange is disposed beneath the subcuticular fascia.

A series of fenestrations in the flange promote anchoring of the spout in place by in-growth of connective tissue through the openings thus provided. This form of anchoring of the spout is believed to provide particular resistance to twisting forces thereon when the cap or plug is attached or removed.

A series of circumferentially spaced, radial openings are also provided at the proximal end of the spout. The openings are disposed so as to be approximately at the cutaneous layer when the spout is implanted in the body wall. These openings are for guiding sutures which temporary secure a portion of the body duct to the layer of mesh on the inside of the spout, to promote initial growth of the serosa of the body duct into the mesh, and to prevent retraction (stricture) of the body duct during initial healing.

In other more specific embodiments, mesh material is attached to the relatively rigid tubular spout in a manner to overlie the inner surface of the proximal end of the spout as well as the outer surface of the proximal end of the spout. This encourages formation of connective tissue on each of such surfaces, thereby providing a natural seal and also helping to further anchor the prosthesis to the body.

A stoma created according to the present invention may eliminate the need for a pouch or bag, though it does not preclude the use thereof if such use is desired. It also retains a liquid and gas in a manner which withstands some pressure and which also allows the patient an opportunity to selectively control voiding through the stoma. Also, it eliminates the need for an adhesive and/or sealant and provides a stoma which can be made liquid and gas tight.

A stoma according to the present invention is further believed to lessen the chances of postoperative herniation and the further surgery required to correct the problem.

A stoma created according to the present invention is still further believed to reduce the possibility of postoperative prolapse and stricture formation.

Additionally, a stoma created according to the invention is believed to alleviate problems of inflammation of the serosa of the body duct by providing biocompatible mesh in contact with the duct at the skin level and adjacent a rigid spout which mesh encourages in-growth of connective tissue from the serosa thus stabilizing the duct and minimizing the irritation leading to serositis, stenosis and formation of scar tissue.

BRIEF DESCRIPTION OF THE DRAWINGS

The invention may be better understood by having reference to the annexed drawings wherein.

DETAILED DESCRIPTION OF THE PREFERRED EMBODIMENTS

Figure 1:
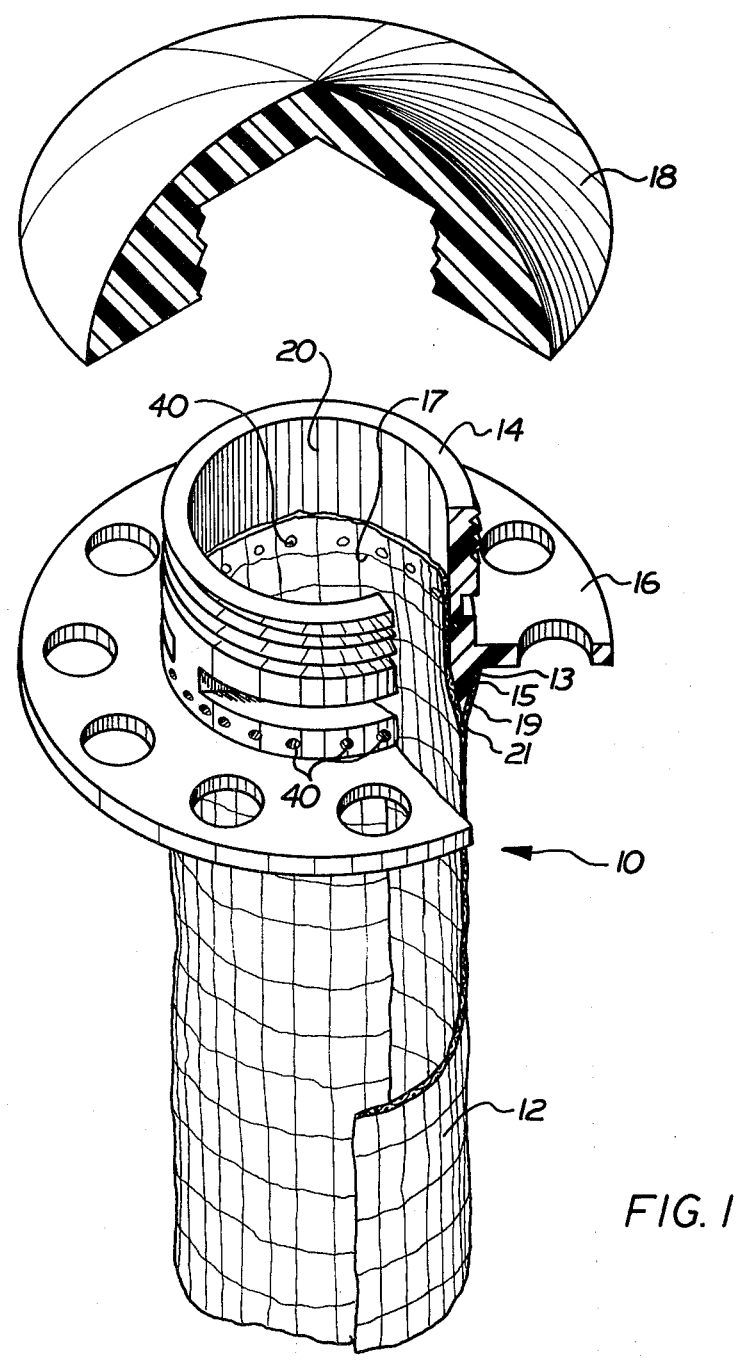
FIG. 1 is partially exploded partially cut away perspective view on an enlarged scale of a prosthesis in accordance with the present invention.

FIG. 1 shows in perspective a preferred embodiment of a prosthesis in accordance with the present invention. The prosthesis 10 includes a flexible longitudinally split sleeve 12 formed of a biocompatible mesh material such as "Marlex" (polypropylene) sold by Davol, Inc. The prosthesis 10 further includes a nonporous relatively rigid tubular spout 14 and a flange 16 integral with the proximal end thereof. The tubular spout 14 and the flange 16 are formed of biocompatible material which may also be polypropylene or other such polyolefin, e.g., polyethylene, a co-polymer of polyethylene and polypropylene, and the like. It has been found that the inclusion of refractory elemental carbon in or on the surface of such biocompatible materials by known procedures enhances the biocompatibility thereof and reduces the chances of rejection by the body.

The term "relatively rigid" as used herein includes but is not limited to sections which are not readily bendable by hand. It also includes structure which, even if it can be flexed by hand, is self-supporting and will not deflect perceptibly when held horizontally by one edge or margin. In general, the relatively rigid sections of the tubular spout 14 are from 1/32–5/32 inch thick.

The sleeve portion 12 is flexible (i.e. pliable by hand). It may be made of substantially any knitted, woven, or heat sealable synthetic or natural fibers that are nonabsorbable and compatible with the animal body, particularly the human body. For example, organic polymeric materials which may be used to form the mesh include silk, cotton, natural and synthetic rubbers, silicones, silastic latex, butyl rubber polymer, vinyl chloride/acrylonitrile, polyamide resins, such as nylon 66, polyacrylonitrile, polyethyleneteraphthalate, polytetrafluoroethylene, polyvinylchloride, polyfluorotrichloroethylene, polyethylene, polypropylene, ethylene-propylene copolymers such as "EPDR" (ethylene-propylene-dicyclopentadiene rubber) urethanes, and the like. "Marlex" knitted polypropylene is an autoclavable mil monofilament mesh material which is especially useful for forming the sleeve 12.

Figure 2:
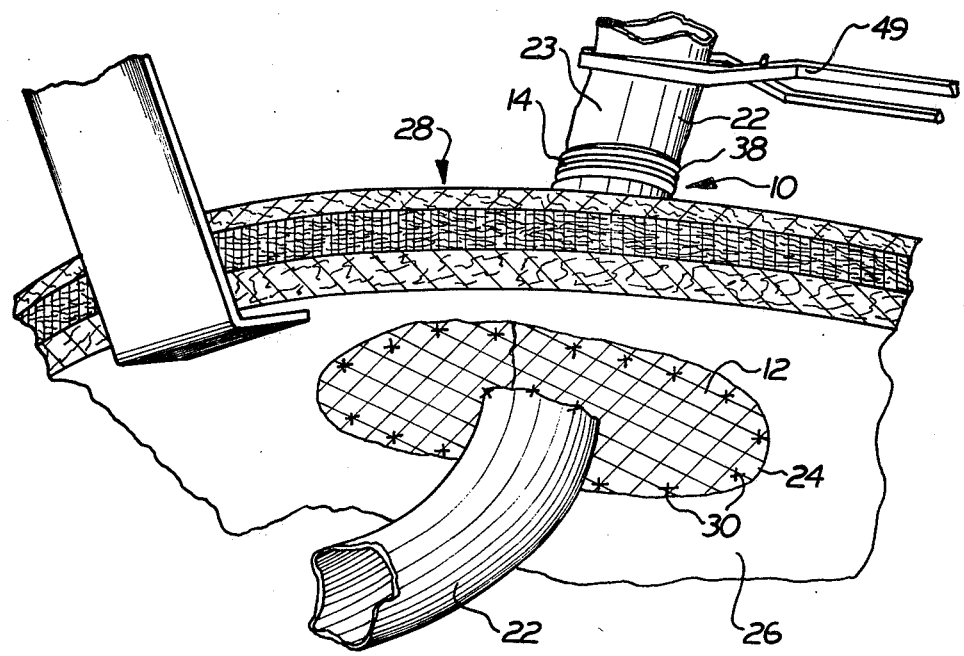
FIG. 2 is an illustration of a mode of attachment of the mesh portion of a device such as in FIG. 1 to the parietal peritoneum.

An advantage of the biocompatible organic polymeric mesh is that when it is wrapped about a body duct such as the colon it promotes in-growth of connective tissue from the serosa surrounding the duct. This has the effect of reinforcing the wall of the duct. The length and width of the mesh forming the sleeve 12 is more than the amount required for use in creating a stoma, e.g., a length of 10–14″ is usually satisfactory. As the stoma is created, excess mesh is cut away and discarded. The mesh sleeve 12 is split longitudinally from the spout 14 to the free end to facilitate wrapping the mesh sleeve 12 around the duct as well as to facilitate creating a patch 24 of the mesh attached to the parietal peritoneum surrounding the opening in the abdominal wall (FIG. 2). For most purposes, a mesh size in the range of 10 to 60 mesh (10–60 openings per lineal inch) will be found suitable.

The relatively rigid tubular spout 14 may be formed of the same or different biocompatible organic polymeric thermoplastic resinous material as that used to form the flexible mesh. The spout 14 may be formed by any suitable plastic shaping means, such as injecting molding. A preferred material from which to form the spout 14 is polypropylene. An advantage of using organic polymer resinous materials to form the spout is that they are tough and tend to make the spout resistant to impact and unlikely to fracture in place.

The mesh sleeve 12 is secured to the spout 14 by any suitable means. Heat sealing is preferred, though use of an adhesive or any other suitable means can be used for attaching the mesh sleeve 12 to the spout. In the preferred embodiment shown in FIG. 1, a cuff portion 13 of the flexible sleeve of mesh material covers a rim 15 at the proximal end of the spout 14.

A layer 17 of mesh is also connected with the inner wall 20 of the tubular spout 14. The layer 17 is disposed inside the spout so that it engages the serosa of a body duct extending through the spout in such a manner that growth of the serosa into the layer of mesh is encouraged. At least part of the layer 17 of mesh is fixed inside the spout, again preferably by heat sealing, to insure that its position is maintained therein.

It is contemplated that the layer 17 of mesh and the portion 13 of the flexible mesh sleeve may also be joined to each other along the circumferential line 21 as by heat sealing.

Figure 3:
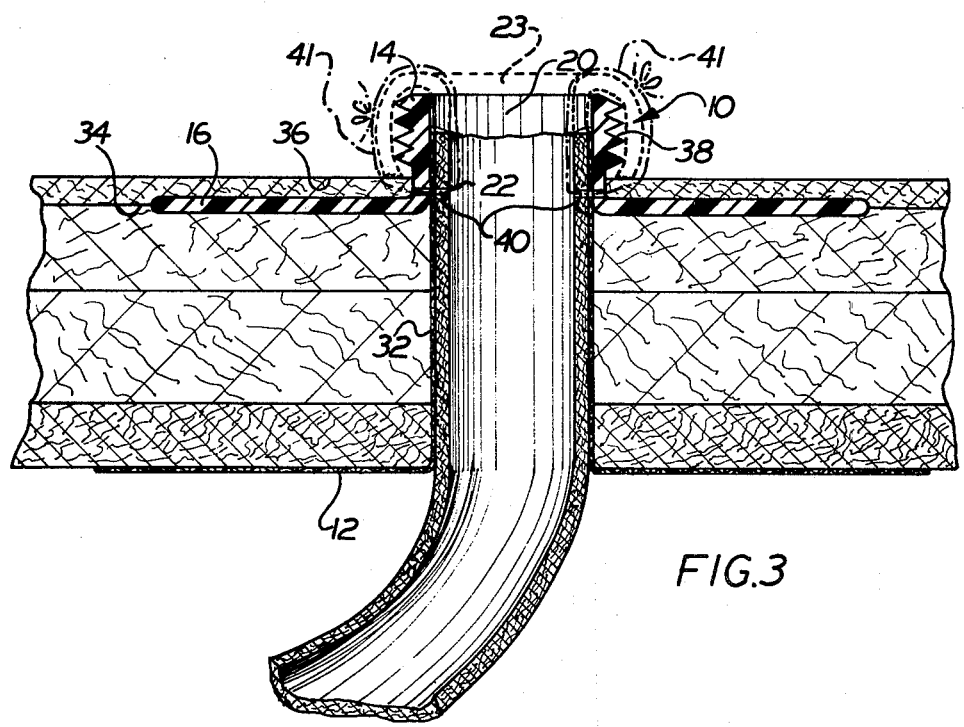
FIG. 3 is an illustration in cross-section of the prosthesis in accordance with the present invention implanted into the body and showing a form wherein mesh material covers the inner and outer surfaces of the spout.

The flange portion 16 is, like the spout 14, relatively rigid and is preferably integral with the spout 14. It is located at the proximal end of the spout 14 and is adapted to extend radially outwardly therefrom. When the prosthesis 10 is implanted in a body wall, the flange 16 is disposed beneath the subcuticular fascia 34 (FIG. 3). As with the sleeve 12 and the spout 14, the flange portion 16 is also made of any of the biocompatible materials mentioned above, preferably polypropylene. Part or all of the flange 16 or the spout 14 may be coated or pigmented by conventional means with carbon to improve the resistance to rejection by the body. The flange portion 16 is intended to lend stability to the device at the cutaneous level, thus lessening the effects of twisting, for example, in applying a cap to the spout 14 and which would contribute to skin irritation and possibly serositis at the site of the the device.

The relatively wide flange 16 also distributes outwardly directed forces as well as inwardly directed forces over a large area thereby minimizing damage due to external impact as well as damage due to intra-abdominal muscular forces which might otherwise cause postoperative herniation in the region of the stoma.

Also shown in FIG. 1 is a cap 18 which is adapted to be threadedly engaged with the distal end of the spout 14 to seal the opening thereof. The cap 18 may also be formed of the biocompatible materials mentioned aboved. Preferably, the cap 18 is formed of polypropylene. Alternatively, a synthetic or natural rubber cap or closure frictionally retained over or within the opening 20 may be used. Biocompatibility of the cap 18, albeit desirable and convenient, is not as critical as with the implanted portions of the device.

The prosthesis 10 also include radial openings 40 extending through the wall of the spout, and a series of arcuate grooves 42 in the outer surface of the spout, for purposes which will become apparent hereinafter.

Referring now to FIGS. 2 and 3, there is here shown one mode of using the prosthesis 10 in a surgical procedure for forming a colostomy stoma in the abdominal wall 28. The stoma is also formed by a body duct 22 which, in the case of a colostomy, comprises a portion of the colon.

As is conventional in the formation of a colostomy stoma, the surgical procedure involves forming an opening in the abdominal wall of the patient, and passing a section of colon through that opening to thereby provide a conduit for directing waste material out of the body. In a procedure according to the principles of this invention a section of the colon 22 is drawn through the inside of the tubular spout 14, and through the opening in the abdominal wall, and the spout 14 is implanted in the abdominal wall such that the proximal end of the spout carrying the flange 16 is immediately below the subcutaneous facia 34. The distal end of the spout 14 protrudes outwardly of the abdominal wall. The holes 40 are disposed about at the base of the spout 14 at the cutaneous level for purposes described more fully hereinafter.

The split sleeve 12 of flexible mesh material is wrapped about the remaining portion of the colon 22 which extends through the opening in the abdominal wall. This causes the mesh to contact th serosa of the colon. A patch-like portion 24 of the sleeve mesh is sutured to the parietal peritoneum 26 surrounding the hole where the colon 22 emerges through the abdominal wall 28. Sutures 30 connect the sleeve portion 24 to the inner side of the parietal peritoneum 26. This assists in maintaining the flexible mesh in contact with the serosa of the colon. Also the patch-like portion 24 of mesh helps resist herniation because it covers the junction of the colon with the opening in the abdominal wall and thus resists body tissue from forcing its way therethrough.

An intermediate portion 32 of the flexible mesh sleeve 12 encircles the colon 22 and engages the serosa of the duct as it traverses through the remaining layer of body tissue of the abdominal wall 28. The mesh sleeve 12 is sutured to any of those additional layers which is practical. This further anchors the colon in place in the opening in the abdominal wall 28. Because of the formation of fibrovascular connective tissue with adjacent tissue, trauma to the colon 22 is minimized.

FIG. 3 shows in cross-section a prosthesis in accordance with the present invention implanted in the abdominal wall and conducting the free end of the duct (colon) 22 to the suface. The flange 16 is disposed immediately beneath the subcuticular fascia 34. The distal end of spout 14 projects outwardly beyond the outer surface 36 of the abdominal wall. In the embodiment shown in FIG. 3, the spout 14 is provided with threads 38 for threaded engagement and sealing with the cap 18.

The colon is drawn through the hole in the abdominal wall and through the inside of the rigid tubular spout 14. A suitable gripping device (not shown) can engage the grooves 42 in the spout to hold the spout firmly in position, and forceps 49 are used to grip the colon 22 to draw the colon through the spout 14 and the abdominal wall. This brings the colon into contact with the layer 17 of mesh on the inside of the spout 14.

The small holes 40 provided in the base of the spout 14 adjacent the cutaneous level (FIG. 3) permit a portion of the colon drawn through the spout to be folded back over the distal end of the spout and temporarily sutured through those holes 40 to the layer 17 of mesh and the portion of the colon inside the spout 14. Thus, the portion of the colon inside the spout is brought into firm contact with the layer 17 of mesh on the inside of the spout 14. The portion of the colon inside the spout then begins to grow into the layer of mesh inside the spout.

After a few days, during which time in-growth of the serosa of the colon into the layer 17 of mesh securely anchors the colon to the spout, the temporary sutures 41 are cut, removed, and the free end 23 of the colon 22 is excized (amputated), either at a point flush with the opening of the spout 14 or at the point where it extends outwardly beyond the layer 17 of mesh within the spout. The free end of the colon 22 will gradually recede to the level of the layer of mesh of the tubular spout 14. The in-growth of the serosa to the layer 17 of mesh will, however, prevent further recession. This is believed to be important in minimizing stricture and contributes to the resistance of the stoma to prolapse. The holes 40 ultimately fill with connective tissue to further stabilize the prosthesis 10. With in-growth of the serosa of the colon into the flexible mesh sleeve 12, prolapse of the colon is further resisted.

Figure 7:
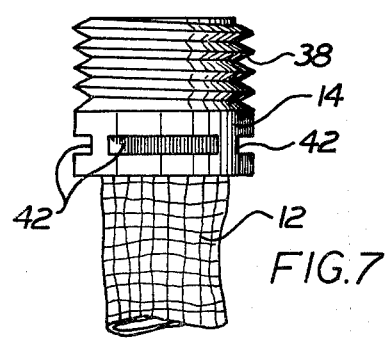
FIG. 7 shows a spout with mesh attached and illustrating the location of slots for facilitating implanting, and holding the spout in use by the patient.

As best shown in FIG. 7, the grooves 42 are designed to be engaged by a tool to permit easy application of the prosthesis 10 and to stabilize it while surgically implanting it, or in applying or removing the capping mechanism. Any other means enabling holding of the device against rotation during implantation or use, including diametrically opposed circular blind recesses or radially projecting nibs may be used as will now be clear. A suitable open end or spanner wrench or fork engageable with diametrically opposed flats 42 or recesses, or nibs, may be used to hold the spout 14 against rotation due to the application of twisting forces.

Figure 4:
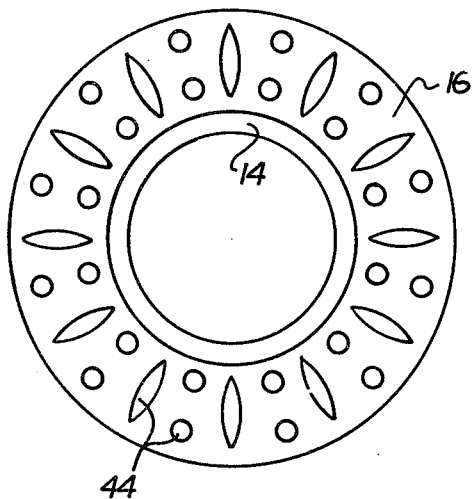
FIGS. 4, 5 and 6 show fenestrated flanges which are useful with the structures of the present invention.
Figure 5:
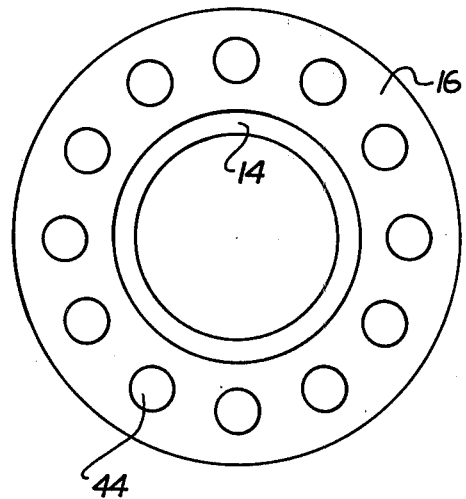
Figure 6:
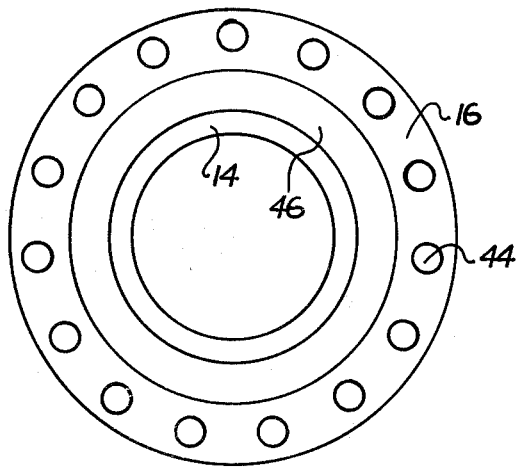

FIGS. 4, 5 and 6 are top views of devices in accordance with this invention and illustrate various forms of fenestrated flanges 16 useful in accordance with the present invention. As indicated above, the flange may be cast integrally with the spout, as shown in FIGS. 4 and 5, for example by injection molding techniques, or frictionally retained about the proximal end of the spout 14 as illustrated in FIG. 6. The openings 44 permit the growth of fibrovascular connective tissue through the flange 16 to securely lock the flange in place and to resist twisting forces. In general, the diameter of a flange should be about 1.5 to 2 times the diameter of the spout. For most purposes, and depending upon the application, the patient, etc., the spout may vary in internal diameter from about 1/10 inch to about 1¼". In the embodiment shown in FIG. 6, the flange is particularly designed to be separate from the spout 14, and frictionally engaged therewith by means of an elastomeric ring 46 disposed around the central opening of the flange, and dimensioned to frictionally engage the outer diameter of the spout 14, or a circumferential ring groove milled or cast into the proximal end of the spout 14. Whether the flanges are integral or separate and fixed to the proximal end of the spout, fenestrations such as shown in FIGS. 4-6 are desirably used.

Figure 8:
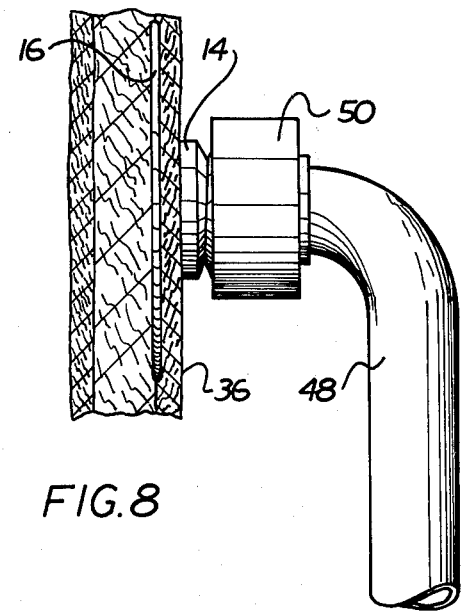
FIG. 8 is an illustration showing attachment of a drainage device to a stoma created according to the present invention.

FIG. 8 illustrates an advantage of the prosthesis of the present invention whereby a tube 48 may be threadedly coupled to the prosthesis 10 by a coupler sleeve 50. This attachment facilitates irrigation or drainage of the colon, ileum, or urethra, as the case may be. Instead of a drainage tube 48, there may be provided a bag attached to the coupler sleeve 50 for threaded attachment of a bag to the prosthesis 10.

There has thus been provided an improved prosthesis and method employing a prosthesis for creating a stoma which provides for the passage of feces, flatus, and/or liquid. The stoma is believed to minimize the likelihood of post operative complications requiring post operative surgery. The stoma may be sealed to eliminate undesirable odors such as often eminate from colostomy and ileostomy stomas. With a stoma created according to the present invention the need to wear a pouch or bag-like device to collect solids or liquids, and the need to use belts, adhesive and sealing materials which often irritate the skin about the stoma may be eliminated. Use of a bag may, however, be accommodated, if desirable.

What is claimed is:

1. A prosthesis for implantation in a body wall for cooperating with a body duct to provide a stoma, said prosthesis comprising a flexible sleeve of biocomptible mesh material for being wrapped about a portion of a body duct passing through an opening in the body wall, a relatively rigid tubular spout of nonporous biocompatible material having a proximal end connected with said sleeve, said relatively rigid tubular spout having a distal end and being dimensioned such that when said proximal end is implanted in the opening in the body wall said distal end protrudes outwardly of the body wall, and a flange of biocompatible material surrounding the proximal end of the relatively rigid tubular spout for disposition beneath the subcuticular fascia of the body wall when the proximal end of the spout is implanted in the body wall.

2. A prosthesis as defined in claim 1 wherein said tubular spout has an inner wall circumscribing the inside of said spout, and a layer of biocompatible mesh material on the inside of said tubular spout for engaging a body duct passing into said tubular spout when said proximal end of said spout is implanted in the body wall.

3. A prosthesis as defined in claim 2 including a series of openings extending through said tubular spout adjacent the proximal end thereof, said openings disposed to guide sutures for temporarily suturing a body duct on the inside of the spout to the mesh on the inside of the spout.

4. A prosthesis as defined in any of claims 1, 2 or 3 wherein the flange is integral with the spout.

5. A prosthesis as defined in any of claims 1, 2, or 3 wherein said flange is fenestrated to enable connective tissue growth therethrough for locking the flange in place when said proximal end of said tubular spout is implanted in the body wall.

6. A prosthesis as defined in any of claims 1, 2, or 3 wherein the biocompatible material is a polyolefin.

7. A prosthesis as defined in claim 6 wherein the biocompatible material is polypropylene.

8. A prosthesis as defined in any of claims 1, 2, or 3 wherein said tubular spout includes an outer wall defining a series of recesses for coaction with an implement of stabilzing said tubular spout during implantation of said proximal end thereof in the body wall.

9. A prosthesis as defined in any of claims 1, 2 or 3 including closure means for engaging and for cooperating with said distal end of said spout for closing and sealing said distal end of said spout.

10. A prosthesis as defined in claim 9 wherein said distal end of said spout includes external threads, and wherein said closure means includes a cap which is internally threaded for engaging said externally threaded distal end of said spout for closing and sealing said distal end of said spout.

11. A prosthesis as defined in any of claims 1, 2 or 3 wherein said flexible sleeve of mesh material includes a cuff connected with the outer surface of the proximal end of said tubular spout, said flexible sleeve of mesh material also being integrally connected with said layer of mesh on the inside of said tubular spout.

12. A prosthesis for implantation in a body wall for cooperating with a body duct to provide a stoma, said prosthesis comprising a flexible sleeve of biocompatible mesh material for being wrapped about a portion of the body duct passing through an opening in a body wall, a relatively rigid tubular spout of nonporous biocompatible material, said relatively rigid tubular spout having a proximal end designed for implantation in the body wall and said flexible sleeve being connected with said proximal end of said spout for implantation therewith in the body wall, said tubular spout having an inner surface circumscribing the inside thereof, said spout having a layer of mesh of biocompatible material on the inside thereof disposed to engage the body duct to promote in-growth of connective tissue from the adjacent tissue of the body duct and to anchor the body duct in the interior of the spout.

13. A prosthesis as defined in claim 12 including a series of openings extending through the proximal end of the spout means for guiding temporary sutures through the spout to temporarily suture a portion of body duct to the layer of mesh on the inside of said spout.

14. A method of making a stoma in a body wall, comprising the steps of implanting a relatively rigid tubular spout of nonporous biocompatible material in an opening in the body wall such that a proximal end portion of the relatively rigid tubular spout is disposed between the inner and outer surfaces of the body wall and a distal end portion of the rigid tubular spout extends outside of the body wall, passing a body duct through the body wall and into an opening in the spout to bring the serosa of the portion of the body duct passing into the opening in the spout into contact with a layer of mesh of biocompatible material in the opening in the spout, wrapping a flexible mesh of biocompatible material about the portion of the body duct passing through the remainder of the body wall and securing a portion of the flexible mesh to the body wall to maintain the serosa of the body duct in contact with the flexible mesh wrapped thereabout.

15. A method as defined in claim 14 wherein the step of securing the portion of the flexible mesh to the body wall comprises the step of creating a patch-like section of the mesh and securing the patch-like section of the mesh to a section of the inner surface of the body wall which surrounds the part of the opening formed in the body wall.

16. A method as defined in either of claims 14 or 15 including the step of attaching the flexible mesh to the proximal end of the tubular spout before implanting the proximal end of the tubular spout in the body wall.

17. A method as defined in any of claims 14 or 15 wherein the step of passing the body duct into the opening in the spout includes the step of passing the body duct through the opening in the spout and temporarily securing the portion of the body duct on the inside of the spout to the layer of mesh on the inside of the spout to allow the serosa of the body duct inside the opening in the spout to begin to grow into the layer of mesh, and thereafter amputating the portion of body duct outside of the tubular spout.

18. A method as defined in any of claims 14 or 15 including the step of implanting the tubular spout in the body wall in a manner which locates a flanged portion at the distal end thereof immediately under the cutaneous layer of body tissue forming the body wall.

* * * * *

UNITED STATES PATENT AND TRADEMARK OFFICE
CERTIFICATE OF CORRECTION

PATENT NO. : 4,217,664
DATED : August 19, 1980
INVENTOR(S) : Joseph M. Faso

It is certified that error appears in the above-identified patent and that said Letters Patent are hereby corrected as shown below:

Column 9, line 6, change "stabilzing" to --stabilizing--.

Column 10, line 36, after the word "of" delete "the".

Signed and Sealed this

Ninth Day of December 1980

[SEAL]

Attest:

SIDNEY A. DIAMOND

Attesting Officer    Commissioner of Patents and Trademarks